US010262756B2

United States Patent
Ghouri et al.

(10) Patent No.: US 10,262,756 B2
(45) Date of Patent: Apr. 16, 2019

(54) SYSTEM FOR GAP IN CARE ALERTS

(71) Applicant: Humana Inc., Louisville, KY (US)

(72) Inventors: Ahmed Ghouri, San Diego, CA (US); Raghu Sugavanam, La Jolla, CA (US)

(73) Assignee: Humana Inc., Louisville, KY (US)

( * ) Notice: Subject to any disclaimer, the term of this patent is extended or adjusted under 35 U.S.C. 154(b) by 133 days.

(21) Appl. No.: 14/086,652

(22) Filed: Nov. 21, 2013

(65) Prior Publication Data

US 2016/0357910 A1 Dec. 8, 2016

Related U.S. Application Data

(60) Provisional application No. 61/729,130, filed on Nov. 21, 2012.

(51) Int. Cl.
*G16H 10/60* (2018.01)
*G06F 19/00* (2018.01)
*G16H 15/00* (2018.01)

(52) U.S. Cl.
CPC .............. *G16H 10/60* (2018.01); *G06F 19/00* (2013.01)

(58) Field of Classification Search
None
See application file for complete search history.

(56) References Cited

U.S. PATENT DOCUMENTS

| | | | |
|---|---|---|---|
| 5,737,539 A | 4/1998 | Edelson et al. | |
| 5,833,599 A | 11/1998 | Schrier et al. | |
| 5,867,821 A | 2/1999 | Ballantyne et al. | |
| 6,024,699 A | 2/2000 | Surwit et al. | |
| 6,081,786 A | 6/2000 | Barry et al. | |
| 6,151,581 A | 11/2000 | Kraftson et al. | |
| 6,338,039 B1 | 1/2002 | Lonski et al. | |
| 6,421,650 B1 | 7/2002 | Goetz et al. | |
| 8,380,591 B1 * | 2/2013 | Kazenas | G06Q 20/102 705/30 |
| 8,799,204 B1 * | 8/2014 | Nease, Jr. | G06F 19/3481 706/50 |
| 2002/0010595 A1 | 1/2002 | Kapp | |
| 2002/0019749 A1 | 2/2002 | Becker et al. | |
| 2002/0026330 A1 | 2/2002 | Klein | |
| 2002/0029223 A1 | 3/2002 | Rice et al. | |
| 2002/0032582 A1 | 3/2002 | Feeney, Jr. et al. | |
| 2002/0035484 A1 | 3/2002 | McCormick | |
| 2002/0040305 A1 | 4/2002 | Nakatsuchi et al. | |
| 2002/0052760 A1 | 5/2002 | Munoz et al. | |
| 2002/0091546 A1 | 7/2002 | Christakis et al. | |

(Continued)

OTHER PUBLICATIONS

Chen et al, Incidence and Possible Causes of Prescribing Potentially Hazardous/Contraindicated Drug Combinations in General Practice, Jan. 2005, Drug Safety, vol. 28 Issue 1, pp. 67-80.

*Primary Examiner* — Fonya M Long
*Assistant Examiner* — William G Lultschik
(74) *Attorney, Agent, or Firm* — Standley Law Group LLP

(57) ABSTRACT

The present invention is a gap in care alert system for alerting someone associated with a patient (including in one embodiment the patient himself) that a gap in heath care will soon occur or in another embodiment that a gap in care has occurred for the patient based on the occurrence of a triggering event and the absence of a follow-up event occurring. Health insurance claims data may be used in the process to determine gaps in care.

4 Claims, 10 Drawing Sheets

(56) References Cited

U.S. PATENT DOCUMENTS

| | | |
|---|---|---|
| 2002/0095313 A1 | 7/2002 | Haq |
| 2002/0116219 A1 | 8/2002 | Ibok et al. |
| 2002/0122063 A1 | 9/2002 | Weinberg et al. |
| 2002/0143582 A1 | 10/2002 | Neuman et al. |
| 2002/0147615 A1 | 10/2002 | Doerr et al. |
| 2002/0188466 A1 | 12/2002 | Barrette et al. |
| 2005/0144038 A1 | 6/2005 | Tamblyn et al. |
| 2006/0047552 A1* | 3/2006 | Larsen ................. G06F 19/327 705/80 |
| 2008/0046289 A1* | 2/2008 | Compton ............. G06F 19/322 705/3 |
| 2008/0082351 A1* | 4/2008 | Kelley-Hrabe ........ G06Q 50/22 705/2 |
| 2008/0114613 A1 | 5/2008 | VanKirk-Smith et al. |
| 2008/0126117 A1* | 5/2008 | Miller ................... G06Q 10/10 705/2 |
| 2008/0126124 A1 | 5/2008 | Schechter |
| 2009/0094054 A1* | 4/2009 | Perrin ................ G06Q 10/0631 705/2 |
| 2009/0216558 A1* | 8/2009 | Reisman .............. G06F 19/328 705/3 |
| 2011/0161109 A1* | 6/2011 | Pinsonneault ......... G06Q 50/24 705/3 |
| 2012/0303378 A1* | 11/2012 | Lieberman ............. G06Q 50/22 705/2 |

\* cited by examiner

SYSTEM FOR GAP IN CARE ALERTS

CROSS REFERENCE TO RELATED APPLICATIONS

This is a nonprovisional application that claims priority to U.S. provisional patent application No. 61/729,130 filed on Nov. 21, 2012 and is herein incorporated by reference in its entirety.

FIELD OF THE INVENTION

The present invention relates to a system and method for analyzing the potential for gaps in patient care and promptly providing alerts to patients and/or care providers that a gap in care may arise or may have arisen so that actions can be taken before a negative result occurs.

BACKGROUND AND SUMMARY OF THE INVENTION

The health care profession has known that gaps in patient care can lead to worsening health for the patient, and if that occurs there is the potential for much higher costs of health care for the patient. For example, it is known that if a diabetic patient does not follow medical advice with respect to insulin treatment schedules the patient's health may deteriorate. It is also known that if a patient has had surgery and a scheduled follow up visit to the doctor is missed the patient's recovery from surgery may be endangered which may result in the patient having to be readmitted to the hospital. Yet another example is in the area of pharmacies. Patients given renewable prescriptions who fail to renew the prescription for a needed drug may result in the patient's condition worsening.

All of the above scenarios are generally defined as gaps in care. There are many reasons why patients may have gaps in care, ranging from forgetfulness, a life changing event, financial reasons, not taking the care instructions seriously, etc. Whatever the reason may be it is important to alert the patient or other entity concerned with the patient (such as their healthcare provider) of a possible gap in care. Systems and methods have been used to alert various entities of medical information important to convey. For example, U.S. Pat. No. 5,754,111 shows one such system. Systems have been developed that use known medical data about a patient compared to historically collected medical data about drugs, conditions, interactions, contraindications, etc., to improve care for the patient. U.S. Pat. No. 7,809,585 describes such a system and method. The entireties of both of these patents are hereby incorporated by reference herein.

The danger in having a gap in care is that the failure to follow medical instructions can result in undesirable outcomes for the patient. These undesirable outcomes may include a slower recovery, a complete lack of recovery potentially resulting in a chronic condition that could have been avoided, or in some cases, a dangerous worsening of a patient's condition. These results are undesirable for the patient's health but also often result in increased health care costs. Incomplete health care can lead to inefficiencies in care. The public, the news media, and some government agencies have become increasingly concerned about the cost and quality of health care. One set of factors that have been applied to measure the quality of care provided is the Heathcare Effectiveness Data and Information Set (HEDIS). HEDIS was developed by the National Committee for Quality Assurance. In addition to the general increase in public awareness of medical care cost and quality, the HEDIS factors provide additional incentive for medical service and health insurance providers to work to control costs and improve patient care. In addition to HEDIS, the Centers for Medicare and Medicaid Services (CMS) have deployed an additional rating system known as "STAR."

In addition to helping to ensure that the performance in the areas considered by HEDIS and STAR are optimized, solutions that minimize the impact of gaps in care have the beneficial effects of improving the quality of care provided to patients, keeping patients healthy or improving their health, and reducing the cost of medical care.

Today's existing computer technologies allow the gathering and analysis of medical data of a patient's medical history. Today, a patient's medical records are often stored electronically, sometimes in records or files known as electronic medical records or EMRs. EMRs are well known such that details of their formation, updating, storing, sending, and receiving electronically via computer network are not explained herein. This electronic storage provides a repository of patient care information that can be leveraged by the health care system to improve a patient's care and reduce the overall cost of a patient's medical treatment. Methods of leveraging a patient's medical record(s) to reduce gaps in care have been developed but can fall short in their ability to change the behavior of patients when it comes to avoiding gaps in care.

The present invention resides in improvements to the means for developing, generating, and communicating the potential for or the existence of a gap in care for a patient. This is done in such a way as to encourage a change in the patient's behavior sufficiently to cause the patient to take the actions required to eliminate or prevent the gap in care. This communication is also delivered in a manner calculated to minimize the actual time of gap in care or prevent a gap in care from happening in the first place. It is understood that once a gap in care approaches or begins, a lengthy delay in communication may widen the time of a gap in care and in doing so, increase the likelihood of an unfavorable impact on the patient or increase the cost of care required to make the patient well.

Various known means of communication may be useful with the present invention. For example, outbound automated phone dialers in electronic communication with a computer system (such as used by telemarketing companies) may be useful in phoning someone about a gap in care. Known computer automated email servers or texting services may also be used to contact someone about a gap in care. Connected to a computer system that determines when to issue an alert or to send an alert, such known systems can be useful in delivering the alert.

In an exemplary embodiment of the present invention, a computer system analyzing patient medical data detects an approaching potential for gap in care and initiates the generation of an alert message and delivery of a communication containing the message directly to the patient in the form of an automated phone call. A communication directly to the patient serves as an efficient and cost effective method to inform and encourage action to eliminate the gap in care. In another exemplary embodiment of the invention, such a phone call is made to a home health care service which then may attempt to contact the patient by an in-person visit to the patient's residence in order to check on the patient's condition and further encourage the patient to conform to the care recommendations provided by their health care provider. Other means for delivering the alerts will be described in the following detailed description, as will means for generating an alert.

In addition to the novel features and advantages mentioned above, other benefits will be readily apparent from the following descriptions of the drawings and exemplary embodiments.

BRIEF DESCRIPTIONS OF THE DRAWINGS

While the appended claims set forth the features of the present invention with particularity, the invention and its advantages may be understood from the following detailed description taken in conjunction with the accompanying drawings, wherein identical parts are identified by identical reference numbers and wherein:

DETAILED DESCRIPTION OF THE INVENTION

The health care system comprises the interactions of three key entities; health care consumers (patients), health care providers, and health insurance providers. When a patient becomes ill, they visit their primary care physician if they have one. If not, a patient may visit an urgent care facility, emergency room, or as is becoming more common, a nurse practitioner that may have an office located in a grocery or drug store. The fact that a patient may visit any one of these health care providers creates the potential for a multiplicity of medical record locations. In such a three entity system, health insurance providers are in a unique position in that they are the recipient, in the form of claims data, of a comprehensive medical record for those health care consumers (patients) that obtain their health care insurance from the health care provider (referred to as members).

When the patient visits a health care provider, they may receive a diagnosis, a recommended treatment protocol and possibly a prescription for medication. Depending on the disease or condition diagnosed, the health care provider may prescribe one or more medications. If the disease or condition requires additional treatment, the treatment protocol may require follow-up care.

Figure 1:
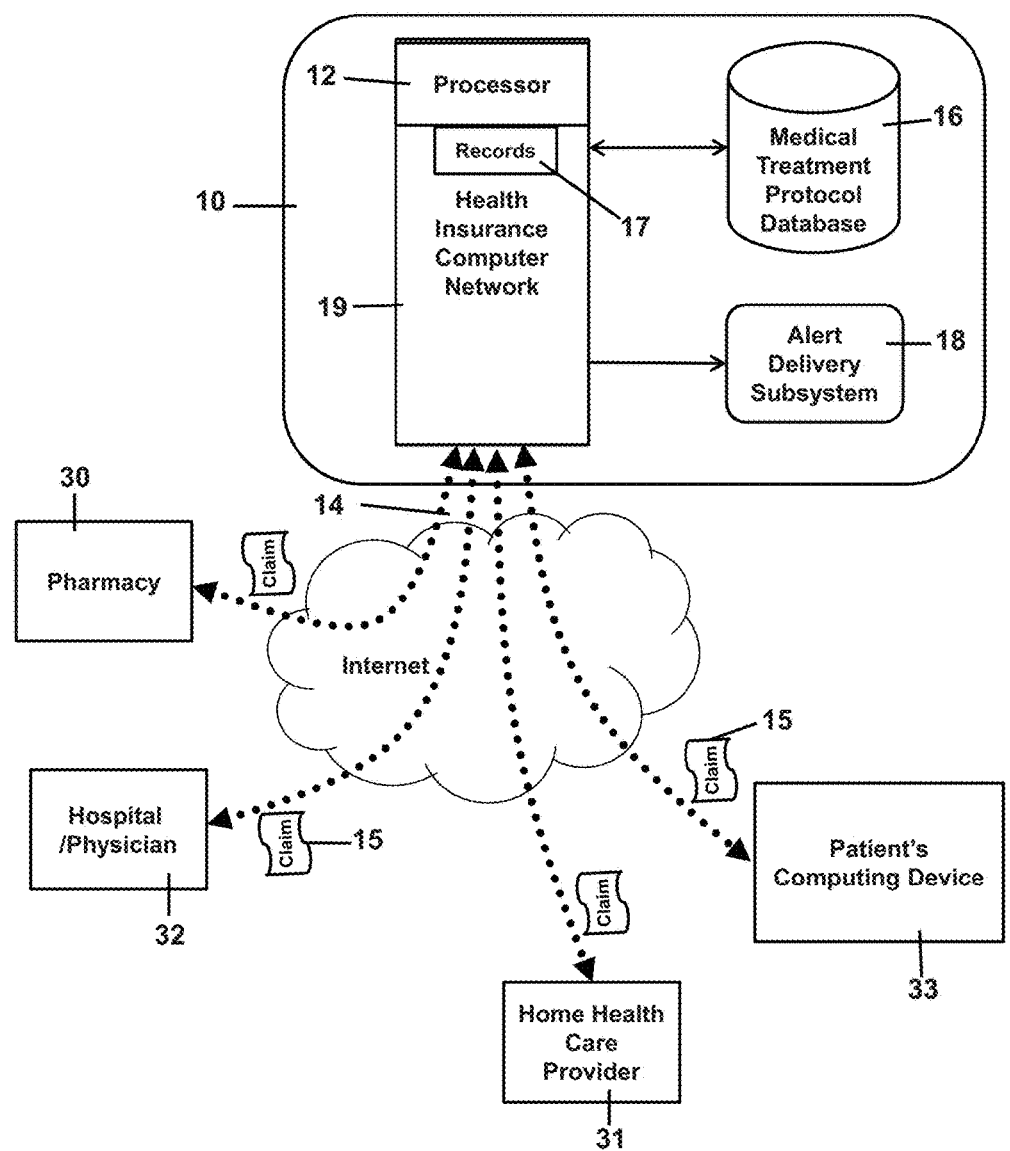
FIG. 1 shows a diagrammatic view of a computer network for use with the present invention.

With reference to FIG. 1 after visiting a health care provider 32, the provider and/or the patient may submit a claim 15 for insurance payment or reimbursement to the patient's health insurance provider 19, for example, via a computer network 14. That claim may contain details of the diagnosis and care provided, along with prescriptions written.

After meeting with the health care provider in a case where a prescription for a drug is written for the patient, the patient may fill a prescription at a pharmacy 30. The pharmacy and/or the patient may generate a claim 15 or report to the patient's health insurance provider 19. This claim may contain information including, for example, identifying information about the patient, the health care provider that generated the prescription, the drug prescribed, the quantity given, and the remaining refills available.

In addition to the patient's primary care physician there are other entities that may be providers of health care to a patient. These may include hospitals, medical specialists, physical therapists, home health care assistants 31, and many other types of care providers. When these additional health care providers perform a health care service for a patient, that provider 31 and/or the patient 33 may submit a claim 15 to the patient's health insurance provider 19 to obtain payment for the services provided. This insurance claim may contain data sufficient to determine a recommended treatment protocol and prescribed follow-up care.

The commonality in each of the previous scenarios is that claims from health care providers are submitted to the patient's health insurance provider. At the health insurance provider, the claim information may be used to process the patient's medical claims and provide payments to the respective service providers according to the terms of the health insurance agreement between the patient and the health insurance provider. This agreement allows the health insurance provider to determine what benefits the patient is entitled to and whether the health care provider is following generally accepted methods of treatment for particular medical conditions.

When a claim is submitted, the patient's claims become part of his or her health record 17 maintained by the health insurance provider on its computer network 19. Because this health record persists after a patient's claims have been paid, the health record serves to gather and maintain information taken from claims submitted by a patient while he or she is served by the health insurance provider. The result is an accumulation of data concerning the patient which may comprise past illnesses, personal data such as age, sex, and ethnicity, vaccine schedules, drugs prescribed, harmful drug reaction, allergies, and family medical history as provided by the patient.

The sheer volume of data and number of patients supported by a health insurance provider requires that in order to perform even the basic function of processing and paying claims that the data be managed by a sophisticated computer system 10 having one or more processors 12 and databases 16. Exposure to a computer system 10 allows the data to be subject to various forms of analysis. One such type of analysis serves as a means to detect gaps in care 20 (see for example, FIG. 3).

In some cases, failure to follow a recommended care regimen may result in a patient not recovering as quickly, suffering from additional illness or disease, or, developing potentially life-threatening complications. For the patient, health care providers, and society, a continued or worsening illness results in frustration, loss of enjoyment of life, potential injury, and when taken in the aggregate, an impact on the productivity of the economy as a whole. A follow-up visit to a primary physician, the resulting prescription cost, and follow-up care costs are just a fraction of what a prolonged recovery or more serious illness may cost in terms of an extended hospital stay that may result if the patient does not follow a prescribed treatment regimen. There is a need for means for prompting the patient to follow a recommended treatment protocol to avoid a situation in which a relatively minor disease progresses to something much more severe, and more costly to treat.

There may be many reasons why a patient does not follow a prescribed treatment regimen. A patient may feel that they are too busy to wait in a health care provider's office for an appointment. A patient may decide that he or she seems to feel better and therefore avoid scheduling a follow-up visit or refilling a prescription to save money. A patient may simply be forgetful or have a medical condition that makes it hard for them to remember and follow instructions. If someone can communicate the potential problems that may result should the patient fail to follow the prescribed treatment protocol, that patient may realize the benefit of follow-up and proceed with their prescribed care. A gap in care system as described herein may provide the information needed to communicate the need for resumption of prescribed care.

Figure 3:
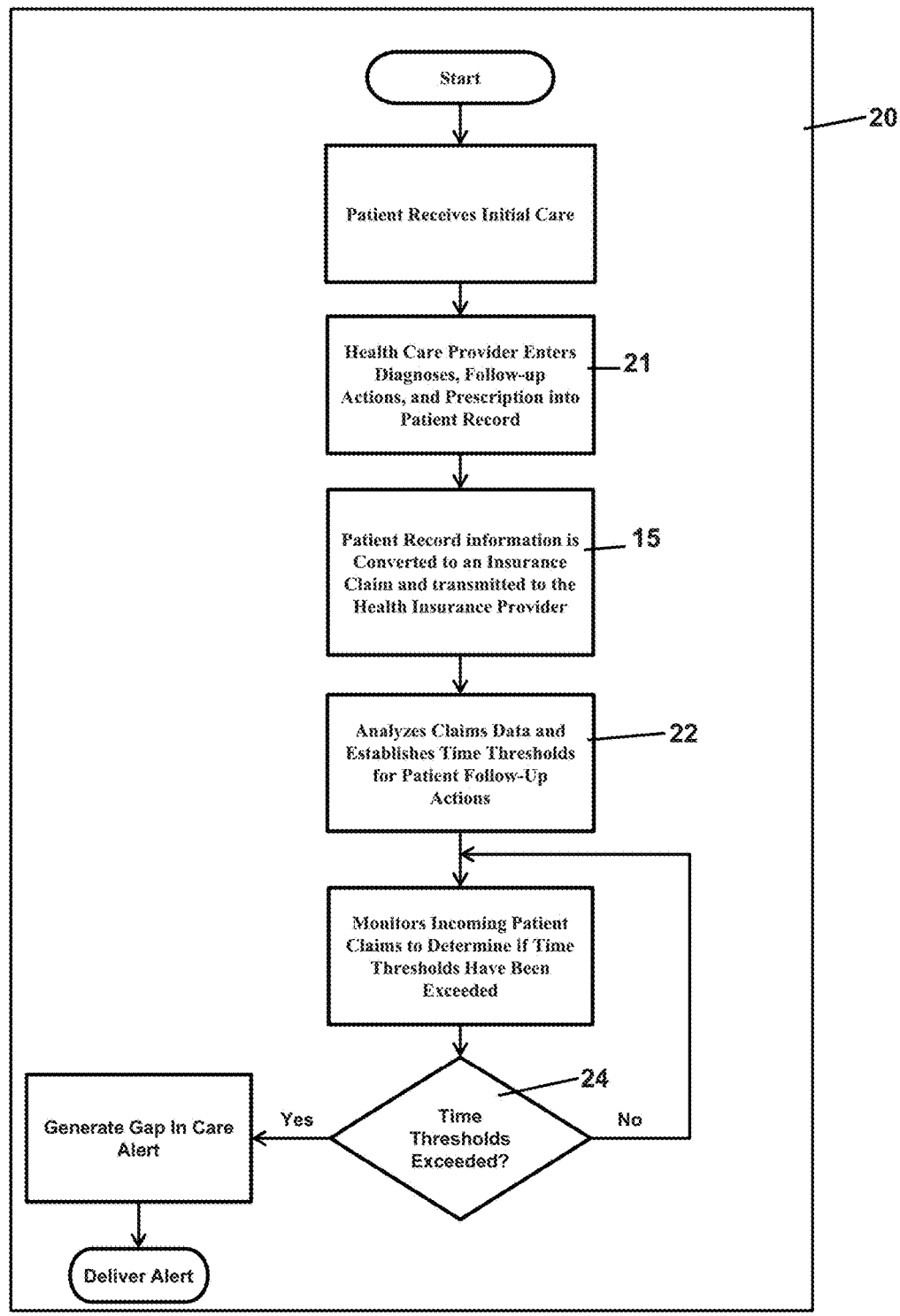
FIG. 3 shows a flow chart of the algorithm of a preferred embodiment of the present invention.

With reference to FIG. 3, a gap in care system 20 of the present invention may be implemented by analyzing a patient's medical treatment 21 and other data in the patient's record, which may be obtained from insurance claims data 15 received at the health insurance company computer network 19. The computerized system automatically identifies upcoming action dates 22, which indicate that a patient is approaching a care event, which if not completed will result in a gap in care 24. For example, using a look-up table of identified and generally accepted vaccination schedules, the system can identify when the patient's last vaccine (if any) was administered and from comparing that to the generally accepted vaccination data in a look-up table forming a part of the computer system 10 the system determines a due date for the next vaccination for that patient. At a predetermined time (which may be selected by the user and input into the system) prior to the due date the system automatically generates an alert to warn the patient of the need to take action and sends it out over the alert delivery subsystem 18 to a patient or someone in connection with the patient. Likewise, numerous other patient care actions may be analyzed and calculated by the system of the present invention. For example, the need for a precautionary colonoscopy by age fifty may be the subject of an alert message to adults of age forty-nine. As another example, an alert advising of the need for an annual wellness physical may be sent each year after a patient's fortieth birthday. Aside from widely implemented care actions (such as vaccines) taken by a large portion of the population, more particular actions of care may be identified on a patient by patient basis from data particular to each patient, stored in the record for each patient in the computer of the system of the present invention. For example, if data on a particular patient indicates a history of high blood pressure, the system of the present invention may be used to alert the patient periodically to the need to have their blood pressure checked. The process of the present invention determines a particular care action date for a patient after which if that particular care is not obtained by the patient an actual gap in care exists; then alerts the patient in advance of the care action date to seek the particular care identified in the alert, and thereby avoid a gap in care.

For the purposes of gap in care analysis and alerts, a health insurance provider is in a unique position. Unlike any single health service provider or primary care physician, the health insurance provider has access to an aggregate of the patient's medical history across practically all forms of health care and sources of that care. For example, a primary care physician may not have a complete record of a patient's care if that patient were to see a health care provider while on vacation in another city or state and that second health care provider failed to deliver a record of the visit or diagnosis to the patient's primary care physician. Another example might be a situation in which a patient provided the incorrect or incomplete name of his primary care physician when visiting an emergency room. Because a patient and/or care provider will very likely seek insurance coverage in every instance of care, the health insurance provider may have the most complete record of a patient's history.

Figure 5A:
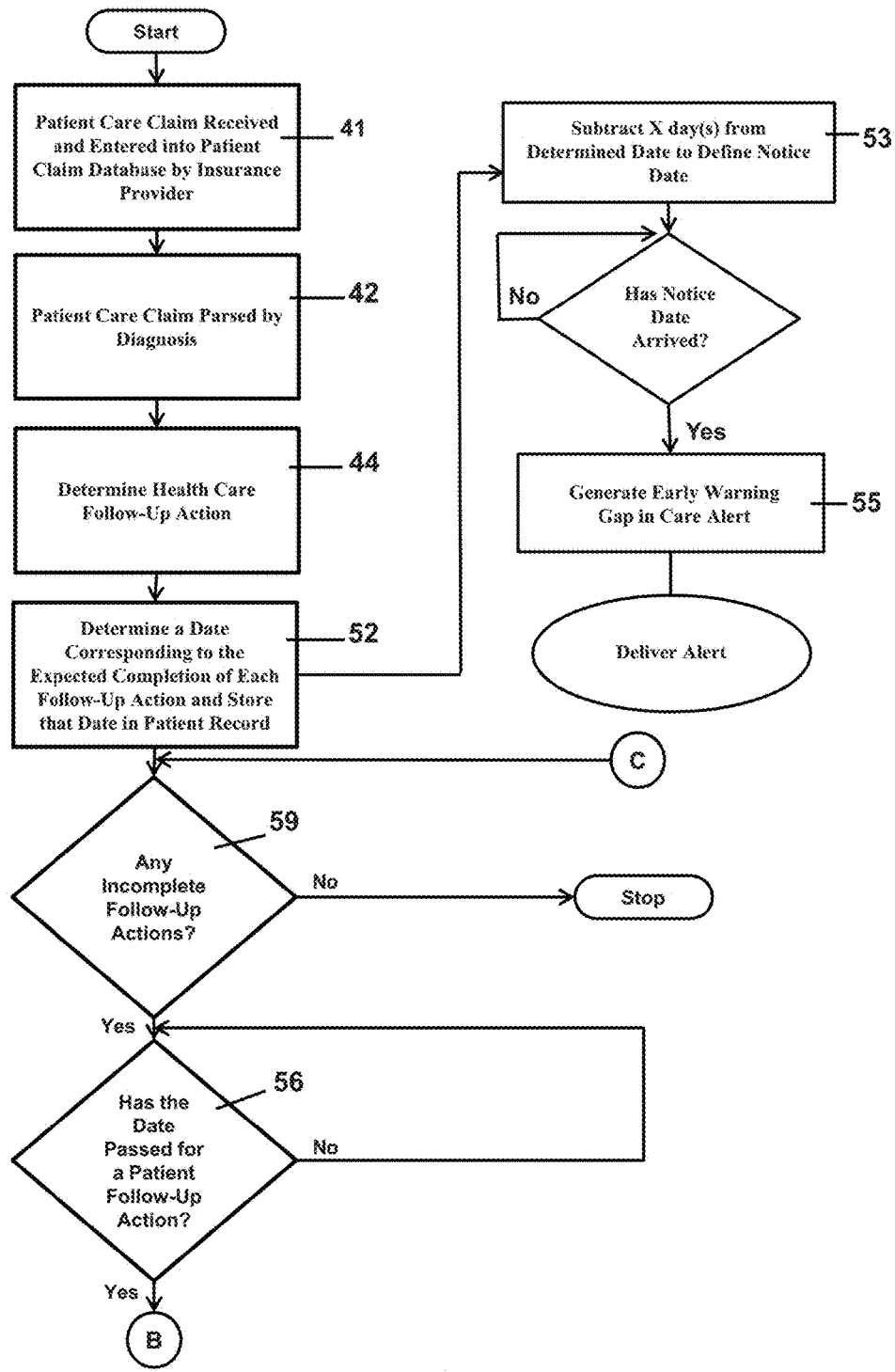
FIGS. 5A and 5B show a flow chart of the follow-up care gap in care detection algorithm for a preferred embodiment of the present invention.
Figure 5B:
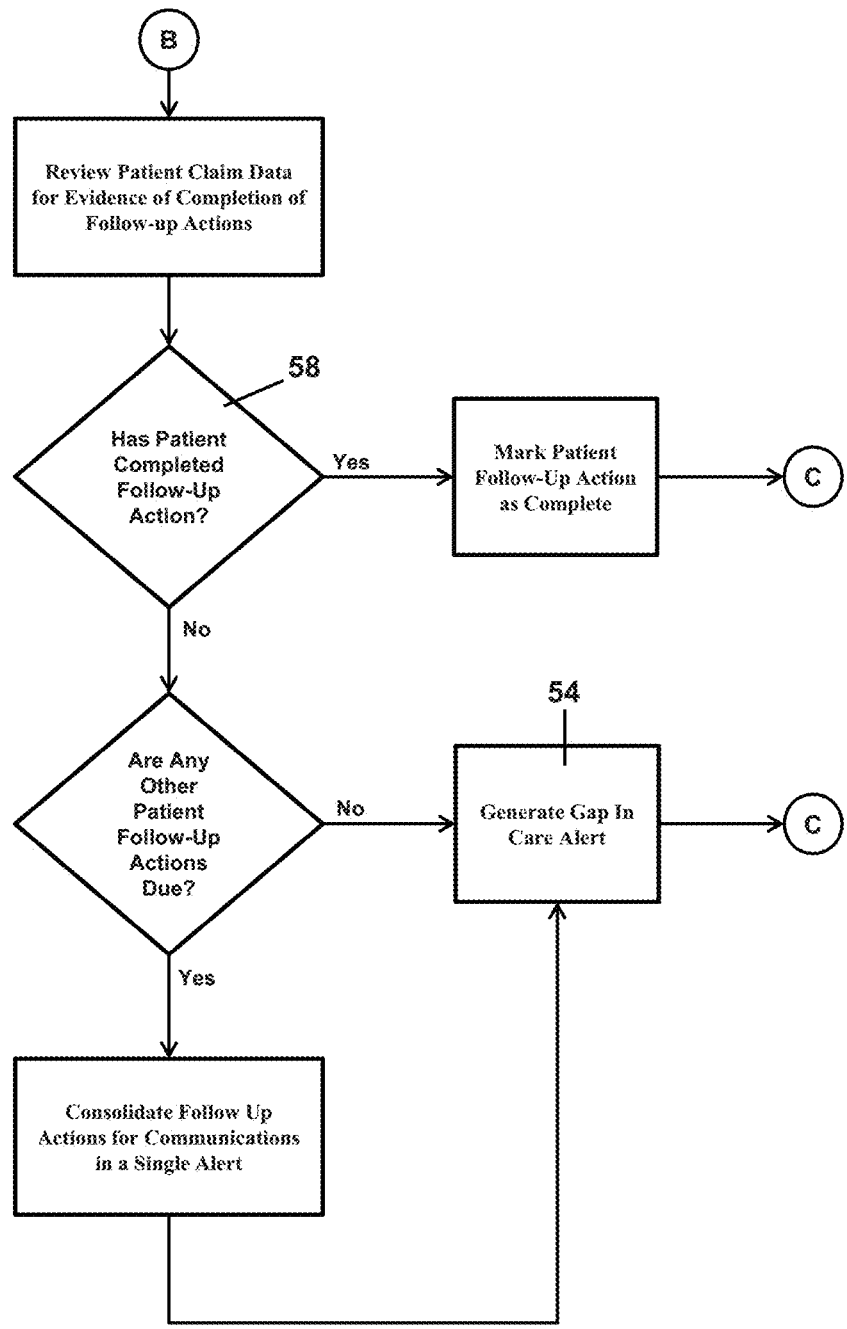

With reference to FIGS. 5A and 5B, to implement a computerized gap in care detection system, claims data received and stored 41 in the record for a particular patient may be analyzed 42 with regard to the type of treatment received, the disease or condition diagnosed, prescription(s) written, and/or the treatment protocol recommended to the patient at 44. A computer algorithm may first check the patient record for a recommended treatment protocol by the health care provider for which the claim was submitted. This may result in the detection of a record detailing recommend follow-up visit(s), prescription medication requirements, or other direction to the patient from the health care provider along with a determined date by which such activity(ies) should occur 52. By subtracting a number of days from the determined date, a notice date is defined at 53. The number of days subtracted may be selected by a user of the system entering the number of days into the program that the user believes is best suited for an early warning of an approaching gap in care. Alternatively, the program may be preset to subtract a particular number of days from the determined date per given diagnosis. Once the notice date arrives, an early warning gap in care alert is generated at 55 and an alert is delivered.

The system may continue to check for whether any follow-up actions have not yet been completed at 59. If so the processor determines whether the date has passed by which a follow-up action was to have occurred, at 56, by reviewing more recently received insurance claims data for the patient. If the patient records show that the patient completed the follow-up action, at 58, the action is noted as being completed in the patient record. If records indicate the patient has not completed the follow-up action a gap in care alert may be generated, at 54. In one embodiment the system surveys for any other follow-up actions the patient has due, and consolidates the communications in a single alert.

Figure 6:
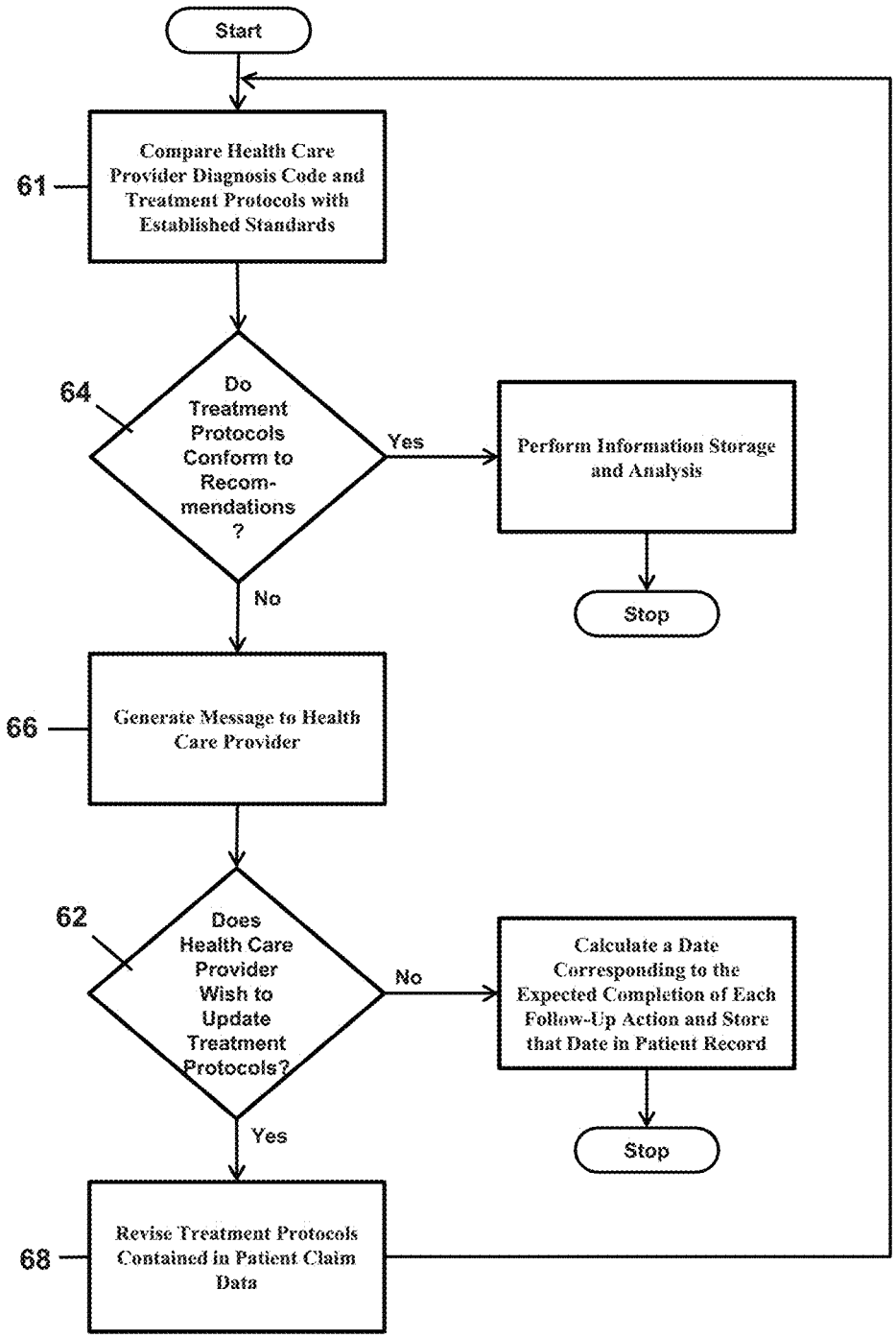
FIG. 6 shows a flow chart of the protocol analysis algorithm of a preferred embodiment of the present invention.

Referring to FIG. 6, a comparison 61 may then be conducted during which health care provider recommendations may be compared to a benchmark set of recommended treatment protocols for the type of illness, condition, or disease diagnosed. Such benchmark protocols may be acquired from a recognized source of such data or may be derived internally by a health insurance provider reviewing historical data for its insured patients over a lengthy period of time. Discrepancies between the results of these analyses may be reviewed by an exception process 62 and revised 68 if necessary to be consistent with established standards. Once the treatment protocol prescribed by the health care provider is checked to see if it is in conformance with the standards for that diagnosis, at 64 it may be analyzed and stored, if not a message may be generated 66 to the health care provider to alert them to the results of the comparison.

Figure 4A:
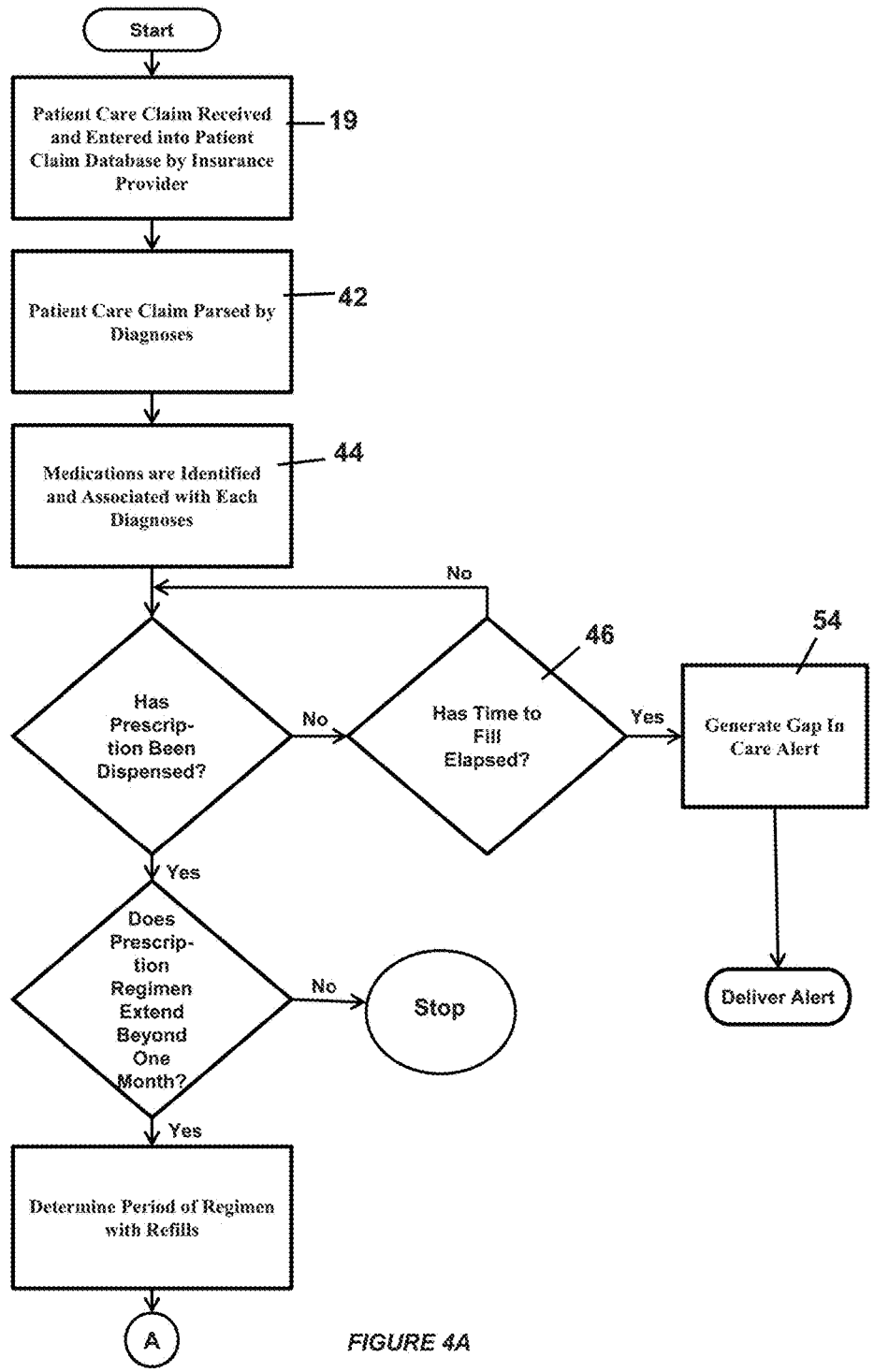
FIGS. 4A and 4B show a flow chart of the gap in care detection algorithm for a preferred embodiment of the present invention.
Figure 4B:
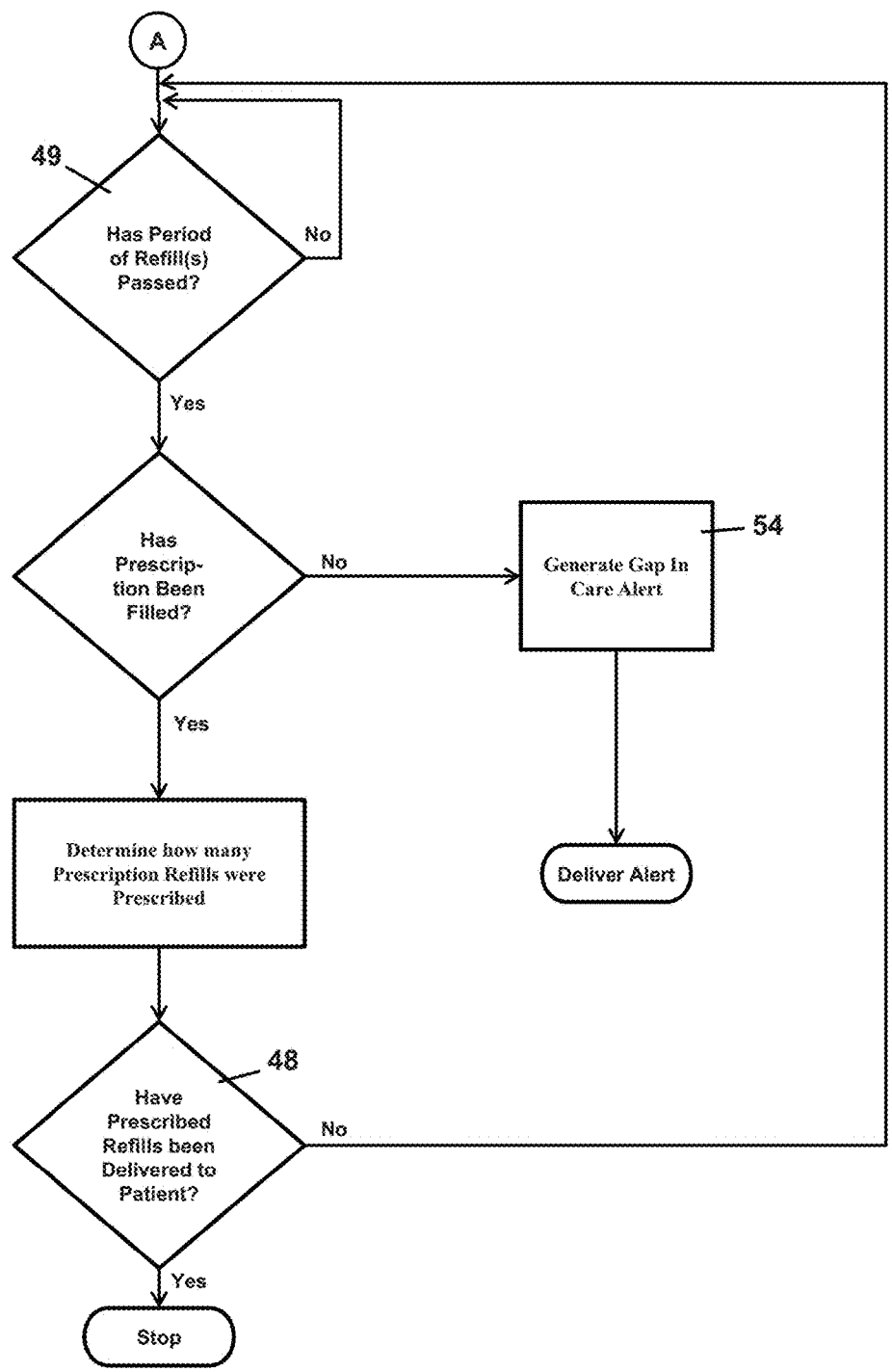

Accordingly, a set of follow-up care requirements may then be established for insured patient claims. Patient follow-up requirements differ depending upon what type of action is required. A first category comprises return visits to the health care provider that performed the initial diagnosis. A gap in care may be indicated if the patient fails to return within an anticipated date for follow up. A second category is that of prescription drugs. FIGS. 4A and 4B show a flow diagram of the computer program algorithm of the present invention for detecting gaps in care caused by a failure to fill drug prescriptions. An insurance claim for a patient is entered 19 into the system and may be sorted by diagnosis code 42. A prescribed medication for the diagnosis may be identified 44. A gap in care alert 54 may be indicated if either of the following conditions is true: a drug has been prescribed to a patient and that patient has not filled the prescription within a calculated time 46 of the drug being prescribed; or a drug has been prescribed with a number of refills and the patient has not refilled the prescription 48 as directed within a time after a refill period 49 as elapsed.

When implementing a gap in care detection system using medical insurance claims, an algorithm may be used to determine what time period elapsed before the gap in care detection system detects that there has been a gap in care. Such an algorithm may be implemented by establishing predetermined periods of time for each type of treatment protocol during which the gap in care detection system will not indicate a gap in care. For example, if a treatment protocol indicates a follow-up action in two weeks the algorithm may be programmed to wait the two weeks plus a predetermined period of days before generating an alert.

Figure 7:
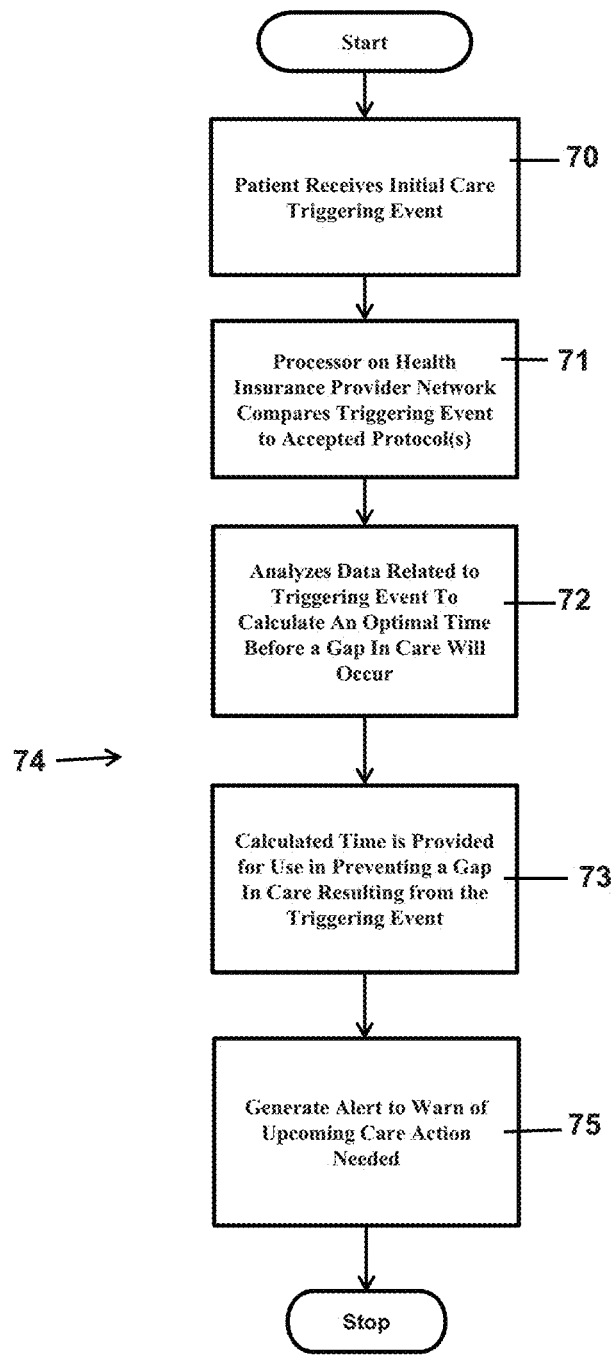
FIG. 7 shows a flow chart of the time to alert algorithm of a preferred embodiment of the present invention.

With reference to FIG. 7 there is shown a flow diagram of a computer program 74 which automatically calculates an optimized date for follow up care and subtracted therefrom would be a number of days (e.g., 14 days) and from the resulting date an alert would be generated and sent automatically to advise the patient in advance of the potential for a gap in care. Such time periods for which a gap in care warning or notification or alert is indicated may be assigned to any triggering event 70. These periods may be calculated based upon analysis of multiple factors, which may comprise the disease, ailment, or surgery suffered by the patient, the treatment protocols prescribed, characteristics and demographics of the patient, statistical analysis of the time generally required to file a particular type of claim, and the historical behavior of the current patient or health care provider with regard to submitting health insurance claims.

A triggering event which starts the clock of the present invention may include but is not limited to, a date of surgery, a date of diagnosis of a disease, a date of treatment beginning, a date an initial prescription for medication is filled, a date of a doctor's office visit by a patient, or practically any other identifiable date from which a subsequent follow up activity should occur. By identifying the specific nature of the triggering event using codes for treatment/diagnosis provided by the health care provider, the processor 12 may access a database of medical treatment protocols 16 to determine the next scheduled follow up event for that triggering event and posts that follow up event date in the computer record associated with the patient. Warnings/alerts may be automatically sent by the system 10 to the patient at a predetermined time in advance of the next scheduled follow up event as a reminder to the patient to avoid a gap in care.

When a triggering event occurs for a patient 70, the processor 12 may perform a comparison 71 based on then-current data, including that data specific to the patient, the patient's disease, ailment, or surgery, and the prescribed treatment protocol applied to the patient's care, in view of generally accepted treatment protocols.

Once a threshold care/triggering event has been determined, the algorithm is then implemented to monitor patient data in the form of claims submitted for follow-up prescriptions and/or care services. For example, a triggering event occurs for a patient (such as knee replacement surgery) on a particular date. An insurance claim is filed for the patient and the health insurance company enters the data from the claim into a computer network. The gap in care detection algorithm of the present invention stores the triggering event in a file associated with the patient's id, for future reference pertaining to follow-up event(s). Next, the present invention preferably automatically determines when a follow-up event should occur for the patient 72, based on, for example, a look-up table of particular health care triggering events (e.g., knee replacement surgery) and time period(s) when associated recommended treatment protocol follow-up events (e.g., follow-up "post-op" visit with the surgeon) should occur (e.g., fourteen days after the surgery date), based on generally accepted medical protocols. The present invention then stores the recommended follow-up event and recommended follow-up event date in the computer network 19, associated with the patient's id. In a preferred embodiment the present invention alerts the patient days in advance 75 of the follow-up event to avoid a gap in care. The present invention preferably includes a clock associated with the computer network that automatically sets a follow-up event date (minus an early warning period) 72 for each triggering event and then tracks that follow-up event date to see if an insurance claim is received for the follow-up event by that date.

Future submitted health insurance claims data may indicate that the patient accomplished the follow up event. If the anticipated date for the follow up event passes and a grace period (or none) passes without receiving an additional claim for that follow up event, the system of the present invention recognizes that there has been a gap in care. Once the system identifies the gap in care an alert signal is actuated automatically by the system and the delivery of the alert is handled automatically by the alert delivery subsystem 18 of the present invention.

Figure 2:
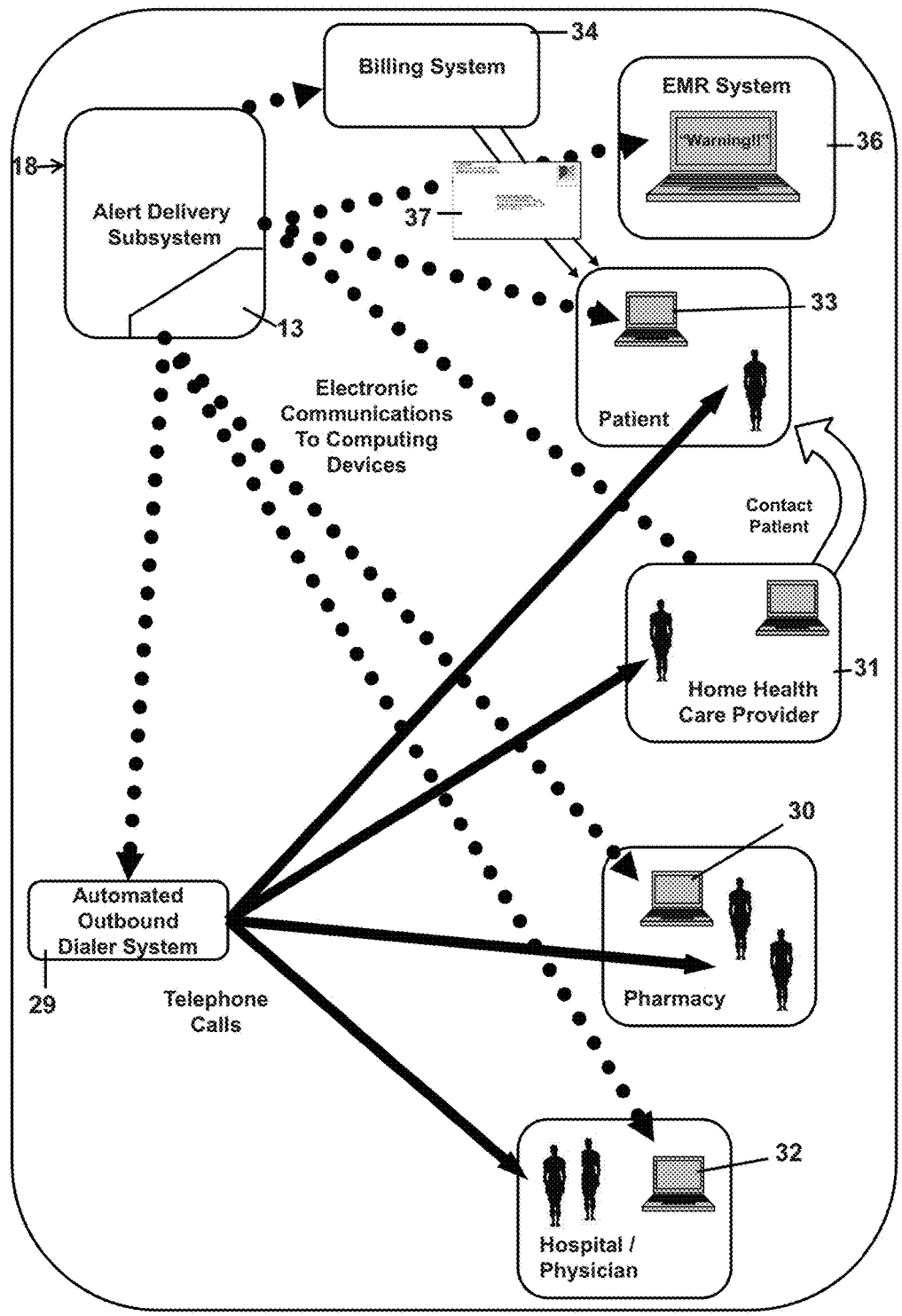
FIG. 2 shows a diagrammatic view of delivery mechanisms for the alerts of the present invention.

Gap in care alerts may be generated by the present invention in advance of and as an early warning to the patient or care provider of an approaching gap in care, or as a notice that an actual gap in care has already occurred. Such alerts may be delivered via an alert delivery subsystem of the present invention, as shown in FIG. 2. The alert delivery subsystem 18 may be configured to deliver the alerts direct to patient devices 33 (e.g., phones, mobile computing devices, home computers, etc.) or to other entities 30, 31, 32, 36 on behalf of the patient (e.g., a health care provider device). The delivery subsystem may use various forms of communications to deliver the alerts (e.g., voice message, text message, email message, warning message to an EMR 36, etc.). The alert message itself may take many forms, including but not limited to: a simple direct informational message that a particular patient follow-up event is upcoming and reminding the patient or health care provider that the patient should perform the follow-up event soon; a robust message describing a particular gap in care and the potential dangers of not accomplishing the follow-up event and a reminder to do so; or a short message indicating that the patient is requested to contact their health care provider or health insurance company representative about an important message for them.

Two examples may be helpful to illustrate the process. In a first example, a claim is submitted that details a follow-up requirement calling for a return visit to the diagnosing physician. The follow-up period is combined with a calculated early warning period. The existence of the requirement for a return visit triggers the gap in care warning algorithm. The algorithm then monitors for claims submitted by or on behalf of the patient for a return visit to the physician. If an insurance claim is not submitted within the calculated time, a potential gap in care may have occurred and is thereby detected. In a second example, a prescription is given to the patient that includes three refills, each with a thirty-day refill period. The claim that contains the record of this prescription triggers the gap in care algorithm. The algorithm monitors the patient's claim data to determine if each refill is done within the refill period plus a grace period. The grace period may be for example about five days on top of the original refill date to allow the patient to visit a pharmacy to obtain a refill. For purposes of this example, if the prescription is not refilled within five days after the refill period, a potential gap in care may exist. As with the first example, the indication that the patient has taken an action in response to a prescribed treatment protocol (refilling a prescription in this example), is the result of a claim to the health insurance provider.

The lack of a claim is an indication that a patient may not have followed a prescribed treatment protocol. The gap in care detection algorithm therefore consists of a means for analyzing patient claims data to detect claims that contain prescribed treatment protocols (sparking a triggering event). When such a claim is detected, the algorithm stores a record of follow-up requirements and calculated completion times associated with the prescribed treatment protocol for a given patient. The system of the present invention then alerts or warns the patient in advance of an approaching gap in care to seek the particular treatment by a particular date or within a particular timeframe. The algorithm then monitors that patient's claims submitted for indications that each of these follow-up requirements has been satisfied. As each requirement is satisfied, the algorithm may remove it from the record of follow-up requirements. If the algorithm determines that a requirement remains in the record of follow-up requirement beyond the expected completion time, an alert may be generated for further action.

The gap in care detection algorithm and analysis process for monitoring claims data are preferably but not necessarily performed on a processor system maintained by the health insurance provider 10. This processor system is connected via a network 19 that houses patient claim data. Various other computer systems may be equipped to access the network including a system for entering claims data 14 into the network, for example over the internet. This claim data entry system may be implemented in a number of traditional ways.

Once the gap in care algorithm identifies a potential gap in care for a patient, the algorithm triggers an alert or early warning. This alert may trigger a further review process at the health insurance provider or alternatively at the health care provider associated with the claim and of the lack of follow-up that caused the gap in care detection algorithm to generate the alert. Once any review is completed, the gap in care early warning may be communicated to an individual or organization by an alert delivery subsystem 18 to follow up with the health care provider or patient. An improvement in gap in care detection comprises a computerized notification system which may be maintained in association with the health insurance provider and connected to the computer network and database which contains patient records and the results of the gap in care detection algorithm's analysis. Referring to FIG. 2, this notification system may be connected to an automated telephone system 29 which when activated by the subsystem 18 generates phone calls to notify patients that a potential gap in care is about to occur or has been detected. This notification system may also include a computerized messaging system 13 capable of sending emails, text messages, or other means of electronic messaging, such means being a rapidly expanding technology such that a person skilled in the art will realize additional possibilities for messaging.

Referring to FIG. 1, health insurance claims data 15 is received by the health insurance computer system 10 and identifies recent medical care provided for a particular patient. If needed or if desired, the computer system may consult medical treatment protocol database 16 to determine the subsequent steps in the treatment of the patient's condition, diseases, ailment, or surgery. The computer system may then determine the next anticipated date for a follow up care event by the patient. Alternative sources may be used for completing the database 16. For example, commercially available treatment protocols may be used, the healthcare provider's treatment protocol may be used, or an in-house generated treatment protocol may be used. Insurance companies are particularly well situated with years of patient healthcare data to know treatment protocols that work well and ones that don't. To help prevent gaps in care the system of the present invention automatically generates an early warning alert to the patient or someone connected in some way to the patient, informing the patient or connected person that an upcoming treatment or care action is needed or suggested by a particular date or within a particular timeframe. The alert message preferably includes a brief description of an action to be taken to avoid a gap in care. If the date passes without follow up by the patient a predetermined grace period may be invoked by the system. After the predetermined grace period, if any, and still no follow up by the patient, the system of the present invention automatically generates an alert. Once an alert is generated the computer system invokes the alert delivery subsystem 18 to get the alert to its proper destination.

The alert, once generated by alert delivery subsystem 18, may be delivered over various channels to predetermined destinations. For example the alert may be sent to a billing system 34 within the insurance company for placement of an alert message on a premium invoice 37 normally sent to an insured via regular mail or email. Or the alert may be sent automatically through an email server to a destination email server for alerting a predetermined party of the gap in care via an email message. The alert may be delivered to an electronic medical record (EMR) 36 housed at a health care provider computer system and presented as a written warning near the top of the EMR to be seen by health care professionals and/or a patient. Many methods of delivery of the alert are contemplated by the present invention.

The data used by the health insurance company computer system to determine a gap in care alert may be derived from health insurance claims data, or various other sources, including health care provider data received from heath care provider data systems, patient entered data received directly from the patients/insureds, or from practically any other medical data source, including pharmacies, home health care facilities, etc. The actual alerts generated by the system of the present invention may be in the form of printed words on paper, electronic words in electronic environment such as electronic messages or texts, voice message, or even speech provided from a delivery person direct to the patient or care provider.

In certain embodiments of the invention, a method of detecting gaps in care may be performed by calculating gap in care alert thresholds using selected HEDIS and STAR performance measure rules. An exemplary list of HEDIS and STAR rules is show in Appendix 1 included in this application. In addition to these rules, Appendix 1 also includes a discussion of how such rules may be used to calculate a failure date. In certain embodiments of the invention, this failure date may be used to indicate when a gap in care may occur and provide an alert in advance of this date.

In another embodiment of the invention, a triggering event may be identified using a HEDIS or STAR category. An exemplary triggering event may be a patient reaching 50 years of age. HEDIS performance measure rules indicate that a patient should have colorectal cancer screening procedures starting at age 50 and continuing until age 75. Using this method, if that patient has not had colorectal cancer screening exam upon turning 50 years of age, a gap in care may be generated. In addition, if such an exam has been conducted, the method may detect the occurrence or occurrences of such exams and calculate the latest recommended repeat of such exams. This latest date may be used to set a threshold, beyond which a gap in care may be indicated. An exemplary algorithm of such a method is illustrated in the flow chart of FIG. 8. In step 802 the algorithm determines if the patient is eligible for one of the applicable HEDIS and STAR rules. Using the example previously given, eligibility may be related to a patient reaching a certain age or age range. If the patient is not eligible based on the appropriate eligibility requirements, in step 804 the algorithm determines if the patient will be eligible before the algorithm is run again in the future. If not, there is no applicable threshold and no gap in care would be detected for the HEDIS or STAR rule being analyzed by the algorithm. If step 804 determines that the patient will be eligible before the next run of the algorithm, step 804 assumes that the patient is eligible and performs step 806. If in step 802 the patient is determined to be eligible, the algorithm continues with step 806. In step 806 the algorithm determines if the patient has a condition that triggers the rule. Using the previous example, a condition may be that a patient has had prior colorectal cancer screening procedures performed. Certain patients that may satisfy eligibility requirements in step 802 may not have any related conditions that trigger a possible gap in care. In such a situation, the algorithm executes step 808 and indicates that there is no applicable threshold and no gap in care would be detected for the HEDIS or STAR rule being analyzed by the algorithm.

Figure 8:
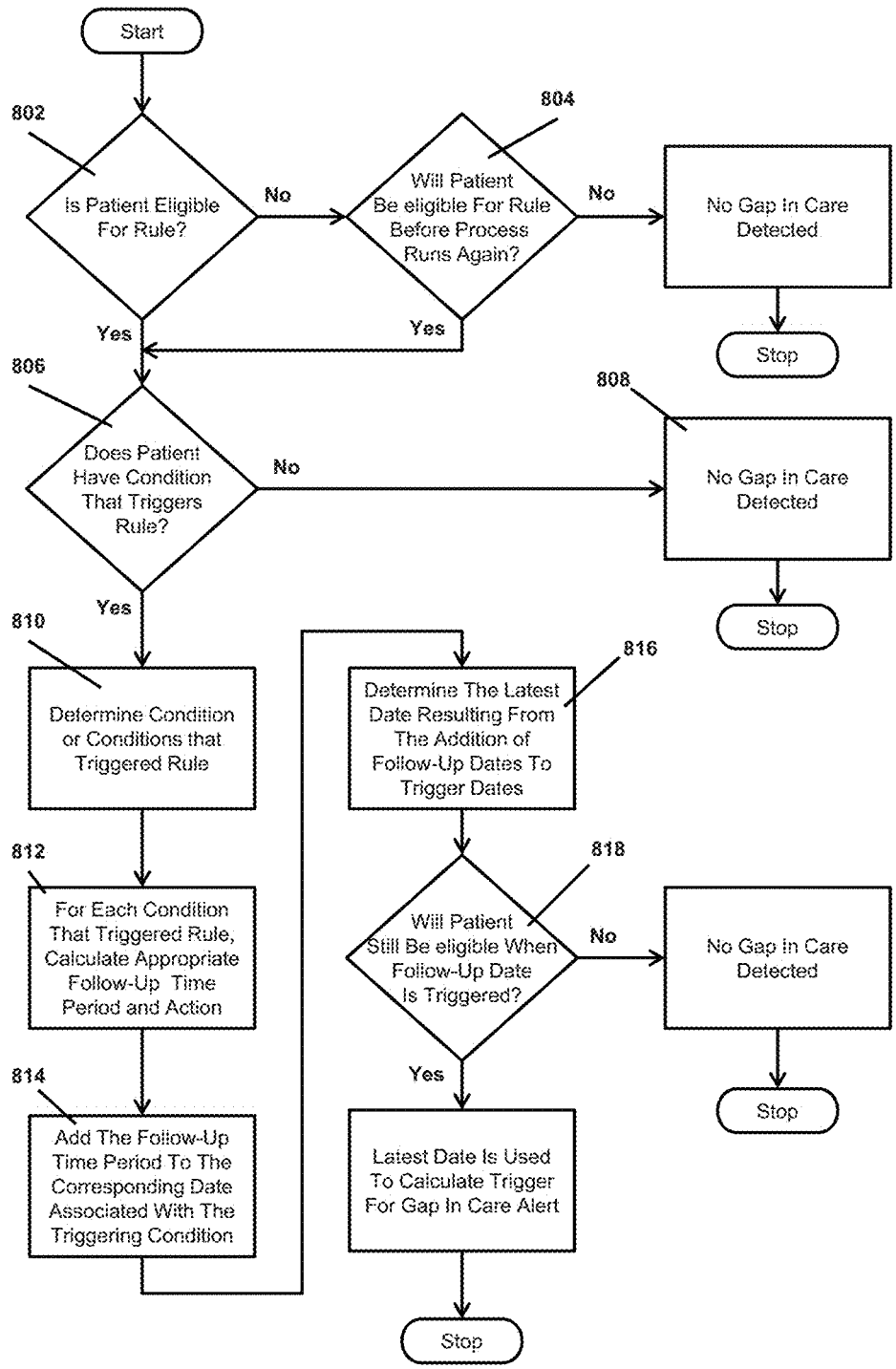
FIG. 8 shows a flow chart of an example process of the present invention for calculating the time threshold that indicates a potential gap in care.

Once the algorithm illustrated in FIG. 8 has determined that a patient has a condition that may trigger the applicability of a HEDIS or STAR rule, step 810 identifies the condition or conditions. Step 812 uses HEDIS or STAR rule data to calculate the appropriate follow-up time period for each condition. Using such rule data insures that time periods are identified that comply with HEDIS and STAR requirements. In step 814 the follow up time periods are added to the dates corresponding to the conditions to which the time periods apply. The result may be a list of conditions and applicable follow up dates. In step 816 the algorithm determines the latest date from those dates derived in step 814. In certain situations a patient may no longer be eligible for the analyzed HEDIS or STAR rule when the latest date is reached. An example may be a colorectal screening requirement that is only applicable until age 75. In such an example, if the patient were to exceed 75 years of age before the identified date, step 818 would indicate that there is no applicable threshold and no gap in care would be detected for the HEDIS or STAR rule being analyzed by the algorithm. If the patient is determined to still be eligible at the latest follow up date, step 820 identifies applicable gap in care threshold as the latest follow up date as identified in step 816.

The present invention has been described herein with reference to the figures and various preferred embodiments, but is not to be construed as limited thereto. The invention is susceptible to modifications and variations that fall within the following claims. The claims of the present invention are not limited to the embodiments described in detail herein but are intended to have broad scope to capture the full scope of the present invention as allowed by law.

APPENDIX 1

What follows is a description of an example alert in advance of a failure date (or date at which a gap in care occurs):

The National Committee for Quality Assurance has developed a set of factors commonly referred to as the Heathcare Effectiveness Data and Information Set (HEDIS). In addition to HEDIS, the Centers for Medicare and Medicaid Services (CMS) have deployed an additional rating system known as "STAR." Selected HEDIS and STAR performance measure rules may be used to calculate an expected time period between a triggering event and the completion of an expected follow up event. Modifications may be made to known, selected Healthcare Effectiveness Data and Information Set ("HEDIS") performance measures rules to compute the Failure Date as defined in each rule. Logic to compute Failure Date may be incorporated into selected STAR Measure rules.

The following logic matrix defines when eligibility and category conditions may trigger the calculation of Failure Date:

| | Compliant | Non-Compliant |
|---|---|---|
| Interested in Failure Date (FD)? | a. Now<br>b. By End of Measurement Year | a. Now<br>b. By End of Measurement Year |
| Eligible for Rule (today) | a. Yes<br>b. No | a. No<br>b. Yes |
| Not Eligible For Rule (today) | a. N/A<br>b. No | a. N/A<br>b. Yes |

In order to illustrate how the Failure Date is calculated, a number of scenarios are presented using the Colorectal Cancer Screening rule as an example. This rule targets adults aged 50-75 years of age, and determines compliance based on the presence of one of 3 different tests. The rule defines the insurance coverage history required for the member to be considered for the rule. These requirements are summarized below.

| Denominator | Numerator |
|---|---|
| 49 > Age < 76<br>Continuous enrollment in the measurement year and the year prior, with no more than 1 gap of less than 46 days in the measurement year or previous year. | One of:<br>FOBT in the past 12 months<br>sigmoidoscopy in past 5 years<br><br>colonoscopy in past 10 years |

Use Case 1:

Member is currently eligible, and compliant with the rule.

Check 1—Will the member still be eligible by the end of the measurement year? (If they will they turn 76 by the end of the measurement year, then no Failure Date will be calculated.)

Check 2—Look for the LATEST service date of EACH of the tests which would satisfy the numerator, and add the appropriate test frequency. The Failure Date would be the latest of these dates. For example, if a member had an FOBT 11 months ago, and a colonoscopy 4 years ago, the Failure Date would be the 10$^{th}$ anniversary of the date of the Colonoscopy.

Use Case 2:

Check to see if the member's age is within one year of the required age, i.e. is the member currently aged 49? Will the member meet the age requirement by the end of the measurement year? If yes, note the date the member will meet the 'age-in' requirement.

Check to see if the member will meet the Coverage requirement by the end of the measurement year. If yes, note the date the member will meet the 'coverage eligibility' requirement.

If the member will be eligible before the end of the measurement year, look for the LATEST service date of EACH of the tests which would satisfy the numerator, and add the appropriate test frequency. The Failure Date would be the latest of these dates and the age-in and coverage-in dates above.

For example, if a member had never received any colorectal cancer screening, had been continuously eligible for 2 years, and will turn 50 between now and the end of the measurement year, the Failure Date is the date the member turns 50.

1) Set the Failure Date to the day of birth in this year.
2) Set the status of an alert record to a new status (e.g., 10), to indicate that this is not an active alert, but that it will become active in the future (the day of birth).

For example, if a member will turn 50 between now and the end of the measurement year, and had an FOBT 11 months ago, the Failure Date would be the later of the 2 dates.

Failure Date should be set outside of the measurement year when the failure date is calculated on an Alert which is currently active and compliant, i.e. anniversary of colonoscopy is 10 yrs in the future.

Failure Date should not be set outside of the measurement year when the Failure Date is calculated on an Alert which is not currently active, but will become active within the current measurement year, i.e. member ages into eligibility or meets coverage requirements within the measurement year.

If on a subsequent analysis a previously computed failure date should be updated, this may be handled as follows:
1) Update existing, compliant and active (status=1) Alert Summary record,
   a. Failure Date can be overwritten with a date further out into the future (i.e. no history of previous failure dates retained).
2) Update Future Failure Date Alert Summary record (status=11)
   a. Failure Date could be updated to a date further out into the future if the alert is not yet active
   b. When the alert becomes Active:
      i. create a new Alert Summary record (status=1)
      ii. retire the previous 'future failure date' record by setting the status to 12
   c. If the rule is turned off
      i. retire the 'future failure date' with a status of 13 (analogous to normal alerts being retired with a status of 3).

Determine whether the rule is age dependent. If it is not, check if member is compliant. If compliant, then compute a future failure date. If not compliant, the algorithm exits without an output.

If the rule is age dependent, the member is checked for age eligibility. If eligible, the member undergoes the compliance check as described in the previous paragraph.

If the member does not pass the age eligibility check, the algorithm determines whether the member's birth date is between the run date and the end of the measurement year. If it is, then the member is re-run with a run date equal to the member's birth date and goes through age eligibility check again. If the member fails the eligibility check again, the algorithm exits. If the member passes the age eligibility this time around, the member then goes through the compliance check. The only difference at this point between a member who was age eligible on the original run date and a member who became age-eligible upon advancing the run date is that non-compliance is of interest, in that non-compliance indicates aging in to the rule and that the member should be flagged for possible intervention soon after the age-in failure date. As for a member who was aged into eligibility and who turns out to be already compliant, a failure date is also calculated and stored.

Other Considerations:

Members who were aged into eligibility should not be put into the denominator tally. Members who were found to be compliant upon aging-in should not be put into the numerator tally.

Other Failure Date Use Cases:

Osteoporosis

Once Eligibility is met (i.e. IESD can be determined), Failure Date is IESD+180 days Coronary Artery Disease Failure Date is anniversary of screening.

Diabetes

Diabetics require nephropathy screening within measurement year

Failure Date is one of:

end of next measurement year anniversary of screening test

Rheumatoid Arthritis

Failure Date=end of next measurement year

Prevention and Screening

Failure Date is not-applicable.

Prevention and Screening

Failure Date is end of next measurement year.

E.g. November 15=special date because January 1 minus 45 day gap.

When a 'future failure date' Alert Summary record becomes 'Active', the system may 'retire' the future failure date' alert with a special status (e.g., 11), and create a new alert record as normal.

In the table below are listed HEDIS/STAR rules categories and failure date scenarios that may be applied to a gap in care alert analysis.

List of HEDIS Star Rules for Failure Date

| Category Description | HEDIS ABBRV | HEDIS SPEC TEXT | HEDIS | Rule ID 1 | Rule Description | Standard Run Failure Date Scenarios | Prospective Failure Date Scenarios |
|---|---|---|---|---|---|---|---|
| Colorectal Cancer Screening | COL | The percentage of members 50-75 years of age who had appropriate screening for colorectal cancer. | HEDIS star | 10594 | Adults 50 to 75 years of age who have claims for appropriate screening for colorectal cancer | 1) Age In - DOB 2) 3 Clinical Component- a. Fecal occult blood test (FOBT) during the measurement year b. Flexible sigmoidoscopy during the measurement year or the four years prior c. Colonoscopy during the measurement year or the nine years prior to the measurement year 3) Eligibility Enrollment date | same |
| Breast Cancer Screening | BCS | The percentage of women 40-69 years of age who had a mammogram to screen for breast cancer. | HEDIS star | 10595 | Women 40 to 69 years of age who had a claim for a mammogram to screen for breast cancer during the measurement year or the year prior to the measurement year | 1) Age In - DOB 2) Clinical Component- One or more mammograms during the measurement year or the year prior to the measurement year 3) Eligibility Enrollment date | same |
| Prevention and Screening | GSO | The percentage of Medicare members 65 years and older who received a glaucoma eye exam by an eye care professional for early identification of glaucomatous conditions. | HEDIS star | 10596 | Patients 65 years and older, without a prior diagnosis of glaucoma or glaucoma suspect, who had a claim for a glaucoma eye exam by an eye-care professional for early identification of glaucomatous conditions during the measurement year or the year prior | 1) Age In - DOB 2) Clinical Component- One or more eye exams for glaucoma by an eye care professional (i.e., ophthalmologist, optometrist) during the measurement year or the year prior to the measurement year. 3) Eligibility Enrollment date | same |
| Prevention and Screening | AAP | The percentage of members 20 years and older who had an ambulatory or preventive care visit. | HEDIS star | 10613 | Patients 20 years and older who had an ambulatory or preventive care visit in the past year - Medicare/Medicaid | 1) Age In - DOB 2) Clinical Component- One or more ambulatory or preventive care visits during the measurement year. 3) Eligibility Enrollment date | same |
| Hypertension | CBP | | HEDIS star | 10615 | Patients 18-85 years of age who had a diagnosis of hypertension (HTN) and whose BP was adequately controlled (<140/90) during the measurement year. | N/A - based on lab value | N/A - based on lab value |
| Coronary Artery Disease (CAD) | CMC | The percentage of members 18-75 years of age who were discharged alive for AMI, coronary artery bypass graft (CABG) or percutaneous coronary interventions (PCI) from | HEDIS star | 10617 | Patients 18 to 75 years of age who were discharged alive for acute myocardial infarction (AMI), coronary artery bypass graft (CABG) or percutaneous transluminal coronary angioplasty (PTCA) | 1) Age In - DOB 2) Clinical Component- An LDL-C test performed during the measurement year, as identified by claim/encounter or automated laboratory data. 3) Eligibility Enrollment date | same |

| Category Description | HEDIS ABBRV | HEDIS SPEC TEXT | HEDIS | Rule ID 1 | Rule Description | Standard Run Failure Date Scenarios | Prospective Failure Date Scenarios |
|---|---|---|---|---|---|---|---|
| | | January 1-November 1 of the year prior to the measurement year, or who had a diagnosis of ischemic vascular disease (IVD) during the measurement year and the year prior to the measurement year, who had each of the following during the measurement year. LDL-C screening | | | in the past year or diagnosed with ischemic vascular disease (IVD) in the past two years who have claims for a LDL Screening during the past 12 months | | |
| Diabetes | | | HEDIS star | 10620 | Patients 18 to 75 years of age with diabetes (type 1 and type 2) with the most recent HbA1c >9%. | N/A - based on lab value | N/A - based on lab value |
| Diabetes | CDC | The percentage of members 18-75 years of age with diabetes (type 1 and type 2) who had Hemoglobin A1c (HbA1c) testing. | HEDIS star | 10621 | Patients 18 to 75 with diabetes (type 1 and type 2) who received HbA1c Testing in the last year | 1) Age In - DOB 2) Clinical Component- An HbA1c test performed during the measurement year, as identified by claim/encounter or automated laboratory data. 3) Eligibility Enrollment date | same |
| Diabetes | CDC | The percentage of members 18-75 years of age with diabetes (type 1 and type 2) who had LDL-C screening. | HEDIS star | 10622 | Patients 18 to 75 years of age with diabetes (type 1 and type 2) who had an LDL-C screening test performed in the past 12 months | 1) Age In - DOB 2) Clinical Component- An LDL-C test performed during the measurement year, as identified by claim/encounter or automated laboratory data. 3) Eligibility Enrollment date | same |
| Diabetes | CDC | | HEDIS star | 10623 | Patients 8 to 75 years of age with diabetes (type 1 and type 2) who have claims for an LDL-C test done during the past 12 months and most recent LDL-C <100 mg/dL | N/A - based on lab value | N/A - based on lab value |
| Diabetes | CDC | The percentage of members 18-75 years of age with diabetes (type 1 and type 2) who had medical attention for nephropathy. | HEDIS star | 10624 | Patients 18 to 75 years of age with diabetes (type 1 and type 2) who have a claim for a diabetic nephropathy screening test or evidence of diabetic nephropathy documented in | 1) Age In - DOB 2) Clinical Component- A nephropathy screening test or evidence of nephropathy, as documented through administrative data. 3) Eligibility Enrollment date | same |

| Category Description | HEDIS ABBRV | HEDIS SPEC TEXT | HEDIS | Rule ID 1 | Rule Description | Standard Run Failure Date Scenarios | Prospective Failure Date Scenarios |
|---|---|---|---|---|---|---|---|
| Diabetes | CDC | The percentage of members 18-75 years of age with diabetes (type 1 and type 2) who had eye exam (retinal) performed. | HEDIS star | 10625 | Patients 18 to 75 years of age with diabetes (type 1 and type 2) who have a claim for a retinal or dilated eye exam by an eye care professional (optometrist or ophthalmologist) in the measurement year or a negative retinal exam (no evidence of retinopathy) by an eye care professional documented in claims data in the year prior to the measurement year | 1) Age In - DOB 2) Clinical Component An eye screening for diabetic retinal disease as identified by administrative data. This includes diabetics who had one of the following. A retinal or dilated eye exam by an eye care professional (optometrist or ophthalmologist) in the measurement year, or A negative retinal exam (no evidence of retinopathy) by an eye care professional in the year prior to the measurement year 3) Eligibility Enrollment date **Note sure - can we tell in a claim if negative retinal exam? 30272 CAT2 code, Can we produce failure date? yes | same |
| Osteoporosis | OMW | The percentage of women 67 years of age and older who suffered a fracture and who had either a bone mineral density (BMD) test or prescription for a drug to treat or prevent osteoporosis in the six months after the fracture. | HEDIS star | 10629 | Women 67 years of age and older who suffered a fracture and who had either a bone mineral density (BMD) test or prescription for a drug to treat or prevent osteoporosis in the six months after the fracture. Sister rule of 10710 | 1) Age In 2) event based: Appropriate testing or treatment for osteoporosis after the fracture defined by any of the following criteria. A BMD test (Table OMW-B) on the IESD or in the 180-day (6-month) period after the IESD, or A BMD test (Table OMW-B) during the inpatient stay for the fracture (applies only to fractures requiring hospitalization), or A dispensed prescription (Table OMW-C) to treat osteoporosis on the IESD or in the 180-day (6-month) period after the IESD 3) Eligibility Enrollment date | |
| Rheumatoid Arthritis | ART | The percentage of members who were diagnosed with rheumatoid arthritis and who were dispensed at least one ambulatory prescription for a disease modifying anti-rheumatic drug (DMARD). | HEDIS star | 10630 | Patients 18 years of age and older who were diagnosed with rheumatoid arthritis and who were dispensed at least one ambulatory prescription for a disease modifying anti-rheumatic drug (DMARD) | 1) Age In - DOB 2) Clinical Component- Members who had at least one ambulatory prescription dispensed for a DMARD during the measurement year. 3) Eligibility Enrollment date | same |

-continued

| Category Description | HEDIS ABBRV | HEDIS SPEC TEXT | HEDIS | Rule ID 1 | Rule Description | Standard Run Failure Date Scenarios | Prospective Failure Date Scenarios |
|---|---|---|---|---|---|---|---|
| Geriatrics | | | HEDIS star | 10638 | Patients 65 years of age and older who had a prescription claim for at least one high risk medication per HEDIS list during the measurement year | N/A - No Failure date possible | N/A - based on lab value |
| Prevention and Screening | PNU | The percentage of Medicare members 65 years of age and older as of January 1 of the measurement year who have ever received a pneumococcal vaccine. | HEDIS star | 10707 | Members 65 years of age and older who have ever received a pneumococcal vaccination. | 1) Age In | same |
| Osteoporosis | OMW | | HEDIS star | 10710 | Women 67 years of age and older who suffered a fracture and who had either a bone mineral density (BMD) test or prescription for a drug to treat or prevent osteoporosis in the 7 days after the fracture | 1) Age In 2) event based: IESD + measurement window - OSTEO FX + 6 mth 3) Eligibility Enrollment date | Not to be used in prospective |
| Prevention and Screening | FSO | The percentage of Medicare members 65 years of age and older as of January 1 of the measurement year who received an influenza vaccination between September 1 of the measurement year and the date when the Medicare CAHPS survey was completed. | HEDIS star | 10712 | Members over 65 years old should receive a flu shot after September 1st of the measurement year. | 1) Age In 2) Clinical - Any time in the flu season (need the exact dates) | |
| Diabetes | | | HEDIS star | 10763 | Patients 18 to 75 years of age with diabetes (type 1 and type 2) with the most recent HbA1c >9%. Sister rule of 10620 except no longer requires lab. | N/A - based on lab value | N/A - based on lab value |
| Diabetes | | | HEDIS star | 10764 | Patients 8 to 75 years of age with diabetes (type 1 and type 2) who have claims for an LDL-C test done during the past 12 months and most recent LDL-C <100 mg/dL. Sister rule of 10623 except no longer requires lab. | N/A - based on lab value | N/A - based on lab value |
| Prevention and Screening | AAP | The percentage of members 20 years and older | HEDIS star | 10784 | Patients 20 years and older who had an preventive care | 1) Age In - DOB 2) Clinical Component- One or | same |

-continued

| Category Description | HEDIS ABBRV | HEDIS SPEC TEXT | HEDIS | Rule ID 1 | Rule Description | Standard Run Failure Date Scenarios | Prospective Failure Date Scenarios |
|---|---|---|---|---|---|---|---|
| | | who had an ambulatory or preventive care visit. | | | visit in the past year Medicare/Medicaid | more ambulatory or preventive care visits (Table AAP-A) during the measurement year. 3) Eligibility Enrollment date | |
| Prevention and Screening | ABA | The percentage of members 18-74 years of age who had an outpatient visit and whose body mass index (BMI) was documented during the measurement year or the year prior to the measurement year. | HEDIS star | 10894 | HEDIS measure for commercial, Medicare and Medicaid. ABA - Adult BMI Assessment | BMI during the measurement year or the year prior to the measurement year as documented through either administrative data or medical record review. | |
| Prevention and Screening | COA | The percentage of adults 66 years and older who had Functional Status Assessment | HEDIS star | 10895 | HEDIS measure for Medicare SNP. COA- Functional Status Assessment | 1) Age In - DOB 2) Clinical Component- At least one functional status assessment during the measurement year (Table COA-D). 3) Eligibility Enrollment date | same |
| Prevention and Screening | COA | The percentage of adults 66 years and older who had Medication Review | HEDIS star | 10896 | HEDIS measure for Medicare SNP. COA- Medication Review | 1) Age In - DOB 2) Clinical Component- At least one medication review (Table COA-B) conducted by a prescribing practitioner or clinical pharmacist during the measurement year and the presence of a medication list in the medical record (Table COA-C), as documented through administrative data. 3) Eligibility Enrollment date | same |
| Prevention and Screening | COA | The percentage of adults 66 years and older who had Pain Screening | HEDIS star | 10897 | HEDIS measure for Medicare SNP. COA- Pain Screening | 1) Age In - DOB 2) Clinical Component- At least one pain screening or pain management plan during the measurement year. 3) Eligibility Enrollment date | same |
| Chronic Obstructive Pulmonary Disease (COPD) | SPR | | HEDIS non-star | 10626 | Patients 40 years of age and older with a new diagnosis of or newly active COPD (no prior claims in the 2 years prior to the diagnosis) who have a claim for having received appropriate spirometry testing to confirm the diagnosis in the two years before to 180 days after the diagnosis. Sister rule of 10709 | 1) Age In 2) event based: IESD + measurement window - Spiro FX + 6 mth 3) Eligibility Enrollment date | |

What is claimed is:

1. A system comprising:

a computer network for receiving health insurance claims data for a health insurance provider, wherein said health insurance claims data is generated after an insured patient receives medical treatment from a health care provider, said health insurance claims data being received by said health insurance provider from or on behalf of said health care provider for payment for said treatment that was provided to said insured patient;

a database comprising predetermined medical treatment protocols for a plurality of medical conditions, wherein said medical treatment protocols include time periods for medical treatment follow-up for particular medical conditions, wherein said time periods are determined using performance measure rules selected from the group consisting of: HEDIS and STAR;

at least one computer processor in association with said computer network for analyzing said received health insurance claims data to identify a triggering event for an insured patient, wherein said triggering event is a date when a healthcare provider performs a medical procedure on said insured patient;

said at least one computer processor in electronic communication with said database and an electronic storage device comprising software instructions, which when executed cause said at least one computer processor to obtain an expected date for a follow-up event for said insured patient in response to the identification of the triggering event, wherein said expected date for a follow-up event is determined by associating said triggering event with a selected treatment protocol from said medical treatment protocols, retrieving the associated time period for medical treatment follow-up for the selected treatment protocol and associated medical condition, adding the associated time period and a grace period to the triggering event, and automatically generating a gap in care alert if subsequently gathered health insurance claims data does not indicate that medical treatment follow-up has occurred for said patient by said expected date;

said at least one computer processor configured to automatically deliver said alert electronically to a receiver; and said electronic storage device comprises additional software instructions, which when executed by said at least one computer processor cause said at least one computer processor to receive health care provider recommendations for follow up events, compare the health care provider recommendations against the selected treatment protocol, and generate a message to the health care provider if the received health care provider recommendations do not match the selected treatment protocol, wherein the generated message comprises a prompt to revise the health care provider recommendations to be consistent with the selected treatment protocol.

2. The system of claim 1, wherein:

said receiver is in electronic communication with an electronic medical record system having an electronic medical record stored therein for said insured patient.

3. The system of claim 1, wherein:

said receiver is in electronic communication with said insured patient's personal mobile communications device and said alert is sent in the form of a text message to said mobile communications device.

4. The system of claim 1, wherein:

said electronic storage device comprises additional software instructions, which when executed, cause said at least one computer processor to determine an early warning date by subtracting a predetermined number of days from the expected date for a follow-up event for said insured patient, and automatically generate an approaching gap in care alert if subsequently gathered health insurance claims data does not indicate that medical follow-up has occurred for said patient by said early warning date.

* * * * *